United States Patent [19]

Yamanaka

[11] Patent Number: 5,273,998
[45] Date of Patent: Dec. 28, 1993

[54] PROCESS FOR MAKING AN OPTICALLY ACTIVE 3,4-DIHYDRO-3,4-EPOXY-2H-1-BENZOPYRAN COMPOUND

[75] Inventor: Tsutomu Yamanaka, Nakatsu, Japan

[73] Assignee: Yoshitomi Pharmaceutical Industries, Ltd., Osaka, Japan

[21] Appl. No.: 963,383

[22] Filed: Oct. 19, 1992

Related U.S. Application Data

[62] Division of Ser. No. 698,775, May 13, 1991, Pat. No. 5,177,216.

[51] Int. Cl.$^5$ .............. C07D 493/04; A61K 31/335
[52] U.S. Cl. ............................ 514/455; 546/15; 549/331; 549/345; 549/387
[58] Field of Search .......... 549/414, 416, 331, 345, 549/387; 546/15, 16; 514/455

[56] References Cited

U.S. PATENT DOCUMENTS

| | | | |
|---|---|---|---|
| 4,446,113 | 5/1984 | Evans et al. | 546/16 |
| 4,639,534 | 1/1987 | Curzons | 549/414 |
| 4,783,483 | 11/1988 | Ferro et al. | 549/414 |
| 4,786,742 | 11/1988 | Curzons | 549/414 |
| 5,091,533 | 2/1992 | Belanger et al. | 549/414 |
| 5,191,093 | 3/1993 | Baker et al. | 549/414 |

FOREIGN PATENT DOCUMENTS 0045150 2/1982 European Pat. Off. .

Primary Examiner—Mukund J. Shah
Assistant Examiner—P. K. Sripada
Attorney, Agent, or Firm—Wenderoth, Lind & Ponack

[57] ABSTRACT

The present invention provides an industrially valuable method for preparing an optically active 3,4-dihydro-3,4-epoxy-2H-1-benzopyran compound which is useful as a starting material for an optically active benzopyran compound with antihypertensive, coronary blood flow-increasing activities and the like, provides a diastereomeric ester compound which is useful as an intermediate for said epoxy compound and also provides a use of said diastereomeric ester compound in making of said epoxy compound, and further an optically active benzopyran compound which is useful as medicine.

2 Claims, No Drawings

PROCESS FOR MAKING AN OPTICALLY ACTIVE 3,4-DIHYDRO-3,4-EPOXY-2H-1-BENZOPYRAN COMPOUND

This application is a divisional of U.S. application Ser. No. 07/698,775, filed May 13, 1991, now U.S. Pat. No. 5,177,216.

FIELD OF THE INVENTION

This invention relates to a method for preparing an optically active 3,4-dihydro-3,4-epoxy-2H-1-benzopyran compound, an intermediate therefor, and a use thereof.

BACKGROUND OF THE INVENTION

U.S. Pat. No. 4,446,113, European Patent Publication No. 95316 and European Patent Publication No. 277,612 disclose benzopyran compounds having antihypertensive actions, smooth muscle-relaxant actions and the like. Moreover, European Patent Publication No. 339,562, discloses that the novel benzopyran compounds bearing a N-acyl-N-oxy-substituted amino group or a hydrazine group at the 4-position, possess hypotensive, coronary blood flow-increasing activities and the like.

Recently, in developing a compound having a chiral carbon atom(s) as drug, the corresponding optical isomer (eutomer) has become important from the view point of enhancement of the pharmacological activity, removal of the side effect, lowering of the toxicity, simplification of absorption, distribution, metabolism or excretion or improvement of the solubility and the like.

The optically active benzopyran compounds which are expected to have such improved characteristics are disclosed in, for example, European Patent Publication No. 120,428 and European Patent Publication No. 314,446.

In the above mentioned patent applications, such optically active benzopyran compounds can be obtained as an end product by reacting the corresponding racemate with a chiral isocyanate such as (−)-α-methylbenzylisocyanate, and then resolving the diastereomers thus obtained by chromatography or fractional crystallization. However, such chiral isocyanates are so hardly available that such method is not practical from the industrial point of view.

On the other hand, the method employing an optically active 3,4-dihydro-3,4-epoxy-2H-1-benzopyran compound as a starting compound is disclosed in British Patent Publication No. 2,204,868 and European Patent Publication No. 344,747. In British Patent Publication No. 2,204,868, there is disclosed that optically active 3,4-dihydro-3,4-epoxy-2H-1-benzopyran compounds can be obtained by reacting trans-3-bromo-2,2-dimethyl-4-hydroxy-2H-1-benzopyran-6-carbonitrile with (−)-camphanic acid, subjecting the mixture of the obtained diastereomers to silica gel chromatography and then subjecting each of diastereomers to hydrolysis. However, (−)-camphanic acid itself is very expensive, and further, the resolution operation of diastereomers by chromatography consumes a long period of time, a lot of solvents and carriers. In brief, such operation is expensive and complicate, and is not suitable for resolution on a large scale.

In European Patent Publication No. 344,747, there is disclosed that optically active 3,4-dihydro-3,4-epoxy-2H-1-benzopyran compounds can be obtained by reacting 2,2-dimethyl-2H-1-benzopyran with N-bromosuccinimide and N-benzyloxycarbonyl-L-alanine chloride and then subjecting the obtained (3R,4S)-4-{(2S)-2-benzyloxycarbonylaminopropionyloxy}-3-bromo-3,4-dihydro-2,2-dimethyl-2H-1-benzopyran-6-carbonitrile to cyclization by hydrolysis.

Therefore, the development of a practically useful method for the optical resolution has been desired.

SUMMARY OF THE INVENTION

The object of the present invention is to provide a low-cost and convenient method for resolving, in large amounts for optically active 3,4-dihydro-3,4-epoxy-2H-1-benzopyran compounds which are useful as an intermediate for drugs.

Another object of the present invention is to provide a diastereomeric ester compound which is useful as an intermediate for said optically active epoxy compound.

Another object of the present invention is to provide a use of said intermediate in making of an optically active 3,4-dihydro-3,4-epoxy-2H-1-benzopyran compound, and further an optically active benzopyran compound which is useful as medicine.

DETAILED DESCRIPTION OF THE INVENTION

The present invention relates to a compound of the formula (I):

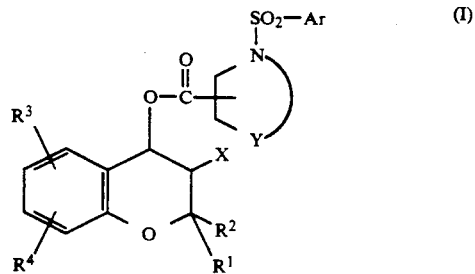

wherein $R^1$ and $R^2$ are the same or different, and each is hydrogen, $C_{1-6}$ alkyl, or $R^1$ and $R^2$ combinedly together form $C_{2-5}$ alkylene; $R^3$ and $R^4$ are the same or different, and each is hydrogen, halogen, nitro, cyano, amino, $C_{1-6}$ alkyl, halo-$C_{1-6}$ alkyl, $C_{1-6}$ alkoxy, halo-$C_{1-6}$ alkoxy, carboxy, $C_{1-6}$ alkoxycarbonyl, formyl, $C_{2-6}$ alkanoyl, halo-$C_{2-6}$ alkanoyl, benzoyl, naphthoyl, phenyl-$C_{2-6}$ alkanoyl, naphthyl-$C_{2-6}$ alkanoyl, formylamino, $C_{2-6}$ alkanoylamino, benzoylamino, naphthoylamino, phenyl-$C_{2-6}$ alkanoylamino, naphthyl-$C_{2-6}$ alkanoylamino, carbamoyl, $C_{1-6}$ alkylcarbamoyl, di-$C_{1-6}$ alkylcarbamoyl, $C_{1-6}$ alkylthio, halo-$C_{1-6}$ alkylthio, $C_{1-6}$ alkylsulfinyl, halo-$C_{1-6}$ alkylsulfinyl, phenylsulfinyl, naphthylsulfinyl, $C_{1-6}$ alkylsulfonyl, halo-$C_{1-6}$ alkylsulfonyl, phenylsulfonyl, naphthylsulfonyl, sulfamoyl, $C_{1-6}$ alkylsulfamoyl, di-$C_{1-6}$ alkylsulfamoyl, in which the term "phenyl", "naphthyl", "benzoyl" and "naphthoyl" include substituted phenyl, substituted naphthyl, substituted benzoyl and substituted naphthoyl by at least one substituent selected from the group consisting of halogen, hydroxy, amino, cyano, $C_{1-6}$ alkyl, $C_{1-6}$ alkoxy and trifluoromethyl on the ring; Ar is phenyl, naphthyl, thienyl, furyl, pyridyl, or substituted phenyl, substituted naphthyl, substituted thienyl, substituted furyl and substituted pyridyl by at least one substituent selected from the group consisting of halogen, hydroxy, nitro, $C_{1-6}$ alkyl, $C_{1-6}$ alkoxy and trifluoromethyl; Y is —N(R)(CH$_2$)$_n$—, —O—(CH$_2$)$_m$—, —S—(CH$_2$)$_p$—, —(CH$_2$)$_q$— (wherein R is hydrogen, C$_{1-6}$ alkyl, phenyl, naphthyl, phenyl-C$_{1-6}$ alkyl and naphthyl-C$_{1-6}$ alkyl; each of n, m and p respectively is integer of 2 to 3 and q is integer of 1 to 3); X is bromine, chlorine or iodine and an optically active compound thereof.

Further, the present invention relates to a method for preparing an optically active 3,4-dihydro-3,4-epoxy-2H-1-benzopyran compound of the formula (II)

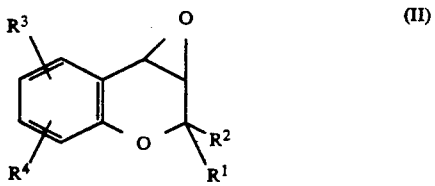

wherein each symbol is as defined above which comprises subjecting a compound of the formula (I) or an optically active compound thereof to cyclization by hydrolysis.

Moreover, the present invention relates to a use of the compounds of formula (I) in making of the optically active 3,4-dihydro-3,4-epoxy-2H-1-benzopyran compound of formula (II) and optically active benzopyran compounds as disclosed in European Patent Publication No. 120,428, British Patent Publication No. 2,204,868, European Patent Publication No. 314,446, European Patent Publication No. 344,747, European Patent Publication No. 339,562 and the like.

In the above-mentioned definitions, halogen means fluorine, chlorine, bromine and iodine; C$_{1-6}$ alkyl means methyl, ethyl, propyl, isopropyl, butyl, isobutyl, tert-butyl, pentyl, isopentyl, hexyl and the like; halo-C$_{1-6}$ alkyl means chloromethyl, bromomethyl, fluoromethyl, iodomethyl, dichloromethyl, dibromomethyl, difluoromethyl, diiodomethyl, trifluoromethyl, chloroethyl, bromoethyl, fluoroethyl, iodoethyl, difluoroethyl, trifluoroethyl, chloropropyl, bromopropyl, fluoropropyl, iodopropyl, difluoropropyl, trifluoropropyl, chlorobutyl, bromobutyl, fluorobutyl, iodobutyl, difluorobutyl, trifluorobutyl and the like; C$_{2-5}$ alkylene means ethylene, trimethylene, propylene, tetramethylene, pentamethylene and the like; C$_{1-5}$ alkoxy means methoxy, ethoxy, propoxy, isopropoxy, butoxy, isobutoxy, tert-butoxy, pentyloxy, hexyloxy and the like; alkoxycarbonyl means methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl and the like; halo-C$_{1-6}$ alkoxy means chloromethoxy, bromomethoxy, fluoromethoxy, iodomethoxy, dichloromethoxy, dibromomethoxy, difluoromethoxy, diiodomethoxy, trifluoromethoxy, chloroethoxy, bromoethoxy, fluoroethoxy, iodoethoxy, difluoroethoxy, trifluoroethoxy, chloropropoxy, bromopropoxy fluoropropoxy, iodopropoxy, difluoropropoxy, trifluoropropoxy, chlorobutoxy, bromobutoxy, fluorobutoxy, iodobutoxy, difluorobutoxy, trifluorobutoxy and the like; C$_{2-6}$ alkanoyl means acetyl, propionyl, butyryl, valeryl, pivaloyl, hexanoyl and the like; halo-C$_{2-6}$ alkanoyl means chloroacetyl, bromoacetyl, fluoroacetyl, iodoacetyl, dichloroacetyl, dibromoacetyl, difluoroacetyl, diiodoacetyl, trifluoroacetyl, chloropropionyl, bromopropionyl, fluoropropionyl, iodopropionyl, difluoropropionyl, trifluoropropionyl, chlorobutyryl, bromobutyryl, fluorobutyryl, iodobutyryl, difluorobutyryl, trifluorobutyryl, fluorovaleryl, fluorohexanoyl and the like; phenyl-C$_{2-6}$ alkanoyl means phenylacetyl, phenylpropionyl, phenylbutyryl, phenylvaleryl, phenylhexanoyl and the like; naphthyl-C$_{2-6}$ alkanoyl means naphthylacetyl, naphthylpropionyl, naphthylbutyryl, naphthylvaleryl, naphthylhexanoyl and the like; C$_{2-6}$ alkanoylamino means acetylamino, propionylamino, butyrylamino, isobutyrylamino, valerylamino, pivaloylamino, hexanoylamino and the like; phenyl-C$_{2-6}$ alkanoylamino means phenylacetylamino, phenylpropionylamino, phenylbutyrylamino, phenylvalerylamino, phenylhexanoylamino and the like; naphthyl-C$_{2-6}$ alkanoylamino means naphthylacetylamino, naphthylpropionylamino, naphthylbutyrylamino, naphthylvalerylamino, naphthylhexanoylamino and the like; C$_{1-6}$ alkylcarbamoyl means methylcarbamoyl, ethylcarbamoyl, propylcarbamoyl, isopropylcarbamoyl, butylcarbamoyl, isobutylcarbamoyl, tert-butylcarbamoyl, pentylcarbamoyl, hexylcarbamoyl and the like; di-C$_{1-6}$ alkylcarbamoyl means dimethylcarbamoyl, diethylcarbamoyl, dipropylcarbamoyl, diisopropylcarbamoyl, dibutylcarbamoyl, diisobutylcarbamoyl, di-tert-butylcarbamoyl, dipentylcarbamoyl, dihexylcarbamoyl, N-methyl-N-ethylcarbamoyl, N-methyl-N-propylcarbamoyl, N-methyl-N-butylcarbamoyl, N-methyl-N-tert-butylcarbamoyl, N-methyl-N-pentylcarbamoyl, N-methyl-N-hexylcarbamoyl and the like; C$_{1-6}$ alkylthio means methylthio, ethylthio, propylthio, isopropylthio, butylthio, isobutylthio, tert-butylthio, pentylthio, isopentylthio, hexylthio and the like; halo-C$_{1-6}$ alkylthio means chloromethylthio, bromomethylthio, fluoromethylthio, iodomethylthio, dichloromethylthio, dibromomethylthio, difluoromethylthio, diiodomethylthio, trifluoromethylthio, chloroethylthio, bromoethylthio, fluoroethylthio, iodoethylthio, difluoroethylthio, trifluoroethylthio, chloropropylthio, bromopropylthio, fluoropropylthio, iodopropylthio, difluoropropylthio, trifluoropropylthio, chlorobutylthio, bromobutylthio, fluorobutylthio, iodobutylthio, difluorobutylthio, trifluorobutylthio and the like; C$_{1-6}$ alkylsulfinyl means methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl and the like; halo-C$_{1-6}$ alkylsulfinyl means chloromethylsulfinyl, bromomethylsulfinyl, fluoromethylsulfinyl, iodomethylsulfinyl, dichloromethylsulfinyl, dibromomethylsulfinyl, difluoromethylsulfinyl, diiodomethylsulfinyl, trifluoromethylsulfinyl, chloroethylsulfinyl, bromoethylsulfinyl, fluoroethylsulfinyl, iodoethylsulfinyl, difluoroethylsulfinyl, trifluoroethylsulfinyl, chloropropylsulfinyl, bromopropylsulfinyl, fluoropropylsulfinyl, iodopropylsulfinyl, difluoropropylsulfinyl, trifluoropropylsulfinyl, chlorobutylsulfinyl, bromobutylsulfinyl, fluorobutylsulfinyl, iodobutysulfinyl, difluorobutylsulfinyl, trifluorobutylsulfinyl and the like; C$_{1-6}$ alkylsulfonyl means methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl and the like; halo-C$_{1-6}$ alkylsulfonyl means chloromethylsulfonyl, bromomethylsulfonyl, fluoromethylsulfonyl, iodomethylsulfonyl, dichloromethylsulfonyl, dibromomethylsulfonyl, difluoromethylsulfonyl, diiodomethylsulfonyl, trifluoromethylsulfonyl, chloroethylsulfonyl, bromoethylsulfonyl, fluoroethylsulfonyl, iodoethylsulfonyl, difluoroethylsulfonyl, trifluoroethylsulfonyl, chloropropylsulfonyl, bromopropylsulfonyl, fluoropropylsulfonyl, iodopropylsulfonyl, difluoropropylsulfonyl, trifluoropropylsulfonyl, chlorobutylsulfonyl, bromobutylsulfonyl, fluorobutylsulfonyl, iodobutylsulfonyl, difluorobutylsulfonyl, trifluorobutylsulfonyl and the like; $C_{1-6}$ alkylsulfamoyl means methylsulfamoyl, ethylsulfamoyl, propylsulfamoyl, isopropylsulfamoyl, butylsulfamoyl, isobutylsulfamoyl, tert-butylsulfamoyl, pentylsulfamoyl, hexylsulfamoyl and the like; di-$C_{1-6}$ alkylsulfamoyl means dimethylsulfamoyl, diethylsulfamoyl, dipropylsulfamoyl, diisopropylsulfamoyl, dibutylsulfamoyl, diisobutylsulfamoyl, di-tert-butylsulfamoyl, dipentylsulfamoyl, dihexylsulfamoyl, N-methyl-N-ethylsulfamoyl, N-methyl-N-propylsulfamoyl, N-methyl-N-isopropylsulfamoyl, N-methyl-N-butylsulfamoyl, N-methyl-N-isobutylsulfamoyl, N-methyl-N-tert-butylsulfamoyl, N-methyl-N-phenylsulfamoyl, N-methyl-N-hexylsulfamoyl and the like; naphthyl means 1-naphthyl and 2-naphthyl; thienyl means 2-thienyl and 3-thienyl; furyl means 2-furyl and 3-furyl; pyridyl means 2-pyridyl and 4-pyridyl.

The compounds of formula (I) can be prepared by reacting a compound of the formula (III)

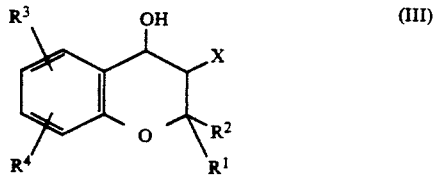

wherein each symbol is as defined above, with a carboxylic acid of the formula (IV)

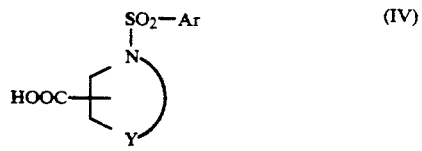

wherein each symbol is as defined above, or the reactive derivative on the carboxyl group thereof.

The reactive derivative on the carboxyl group of the compound of formula (IV) include an acid halide such as an acid chloride, an acid bromide or an acid iodine, an acid anhydride, a mixed acid anhydride with an alkyl-haloformate, and ester such as methyl, ethyl, benzyl or p-nitrobenzyl, a thiol ester and the like.

When either the L-(−) form or the D-(+) form of the compounds of formula (IV) is used in this reaction, the corresponding one of the L-(−) form or the D-(+) form of the compounds of the formula (I) as a single configuration is only obtained.

The compound formula (I) can be prepared by reacting the compound of formula (III) with the compound of formula (IV) in a carboxylic acid form in the presence of a dehydrating agent, for example, dicyclohexyl carbodiimide, N-hydroxysuccinimide, 1-hydroxybenzotriazole, 4-dimethylaminopyridine, carbonyldiimidazole, Vilsmeier agent, tosylochloride-pyridine, phosphorous oxychloride, polyphosphoric acid, dimethylformamide diethylacetal, Mukoyama agent.

It is advantageous for industrial use that the compound of formula (IV) is converted into the corresponding carboxylic acid chloride compound and then allowed to react with the compound of formula (III).

Such a carboxylic acid chloride compound can be prepared by reacting the compound of formula (IV) with, for example, thionyl chloride preferably under reflux in the presence of the solvent such as a haloalkane (e.g. cholorform, methylene chloride, dichloroethane), benzene or toluene.

The object compound of formula (I) as a mixture of the diastereomers can be obtained by reacting the obtained carboxylic acid chloride compound without further purification with the compound of formula (III) under ice-cooling or heating in a solvent (e.g. chloroform, methylene chloride, dichloroethane, benzene, toluene, diethyl ether, dioxane, tetrahydrofuran) in the presence of an acid scavenger (e.g. pyridine, triethylamine, anhydrous potassium carbonate).

The obtained compounds of formula (I) are able to separate into a single form of each isomer by, preferably, fractional crystallization.

Such fractional crystallization can be carried out by using an acetic acid ester (e.g. methyl ester, ethyl ester, butyl ester), a lower alcohol (e.g. methanol, ethanol, propanol), a hydrocarbon (e.g. petroleum ether, hexane, benzene, toluene), a halo-alkane (e.g. methylene chloride, chloroform, dichloroethane), and ether (e.g. diethyl ether, dioxane, tetrahydrofuran), a ketone (e.g. acetone, methyl ethyl ketone), an amide (e.g. dimethylformamide, dimethylacetamide), water or their mixed solvents.

The compounds of formula (IV) as chiral derivating agents and as crystals which are easy to purify can be prepared by reacting either L-(−) or D-(+) astereomers of the formula (V)

wherein each symbol is as defined above, which are industrially available, with phenylsulfonyl halide (wherein a halide is chloride, bromide, fluoride and iodide), naphthylsulfonyl halide, thienylsulfonyl halide, furylsulfonyl halide, pyridylsulfonyl halide, substituted phenylsulfonyl halide, substituted naphthysulfonyl halide, substituted thienylsulfonyl halide, substituted furylsulfonyl halide and substituted pyridylsulfonyl halide by one step reaction.

According to the method of the present invention, the optically active epoxy compound of formula (II) can be obtained by subjecting each isomer of the diastereomer of formula (I) obtained by the above-mentioned manufacturing and separating method to cyclization by hydrolysis, preferably, with addition of an alkali hydroxide (e.g. sodium hydroxide, potassium hydroxide) in a solvent such as water, a lower alcohol, an ether or their mixed solvents.

The reaction of cyclization by hydrolysis can be carried out by stirring at room temperature or under heating. Any epimerization or racemization do not occur in the course of said reaction.

The unreacted compound of formula (IV) as a crystal can be recovered by acidifying the mother alkaline solution which is obtained by filtering off the objective epoxy compound of formula (II) and the recovered compounds can be used in the following reaction with or without purification.

The present invention has the following characteristics.

(1) The compounds of formula (IV) prepared from a low-priced L-(−)-proline are used as chiral derivating agents.

(2) The compounds of formula (IV) used as chiral derivating agents can be removed in a large yield and used in the following reaction with or without purification.

(3) Each isomer of the diastereomer of formula (I) can be obtained by the conventional fractional crystallization.

(4) The thus obtained isomer of the diastereomer can be converted into the corresponding optically active 3,4-dihydro-2,2-dimethyl-6-substituted-3,4-epoxy-2H-1-benzopyran compounds desired industrially by conventional hydrolysis.

(5) Moreover, the objective compounds of formula (II) obtained by the methods of the present invention, can be reacted to the optically active benzopyran compounds which are disclosed, for example, in European Patent Publication No. 339,562 and European Patent Publication No. 120428, and exhibit remarkably long-lasting hypotensive actions and the like.

For instance, European Patent Publication No. 339,562 discloses that (+)-trans-4-(N-acetyl-N-benzyloxy)amino-6-cyano-3,4-dihydro-2,2-dimethyl-2H-1-benzopyran-3-ol, melting at 145°–147° C., as a novel benzopyran compound can be produced by reacting (−)-6-cyano-3,4-dihydro-2,2-dimethyl-3,4-epoxy-2H-1-benzopyran with O-benzylhydroxylamino-6-cyano-3,4-dihydro-2,2-dimethyl-2H-1-benzopyran-3-ol with acetyl chloride and further European patent Publication No. 120428 discloses that (−)-6-cyano-3,4-dihydro-2,2-dimethyl-trans-4-(2-oxo-1-pyrrolidinyl)-2H-1-benzopyran-3-ol (lemakalim; BRL-38,227) can be produced by reacting (−)-6-cyano-3,4-dihydro-2,2-dimethyl-3,4-epoxy-2H-1-benzopyran with 2-pyrrolidone.

The present invention will be concretely explained by the following examples, but they are not construed limit to the scope of the invention.

REFERENCE EXAMPLE 1

To a solution of 12.0 g of sodium hydroxide in 150 ml of water was added 15.0 g of L-proline and dissolved under water-cooling at 15° C. The solution was stirred under water-cooling at 15° C. and to the reaction mixture was added 30.0 g of 3-nitrobenzenesulfonyl chloride and 15 ml of diethyl ether under stirring for 15 minutes. After stirring at room temperature for 80 minutes, the reaction mixture was acidified at pH2 with concentrated hydrochloric acid and the separated oily substance was extracted with ethyl acetate. After the organic layer was washed with aqueous sodium chloride, the solution was filtered and the filtrate was concentrated under reduced pressure. The crystallized residue was boiled with 300 ml of hexane-ethyl acetate (1:1) and was cooled. The obtained crystals were collected by filtration to give 31.7 g of N-3-nitrobenzenesulfonyl-L-proline, melting at 155°–157° C., $[\alpha]^{23}_D = -71.3°$ (c=1, CHCl$_3$)

The following compounds can be prepared in a similar manner mentioned as in Reference Example 1.

N-4-toluenesulfonyl-L-proline, as an oily substance
N-4-nitrobenzenesulfonyl-L-proline, melting at 147°–149° C., $[\alpha]^{23}_D = -69.8°$ (c=1, CHCl$_3$)
N-4-chlorobenzenesulfonyl-L-proline, melting at 107.5°–109.5° C., $[\alpha]^{23}_D = -80.4°$ (c=1, CHCl$_3$)
N-2-nitrobenzenesulfonyl-L-proline
N-2,5-dichlorobenzenesulfonyl-L-proline

EXAMPLE 1

(1) To a suspension of 31.3 g of N-3-nitrobenzenesulfonyl-L-proline and 120 ml of chloroform was added 15 ml of thionyl chloride and the mixture was refluxed under heating for 100 minutes. After completion of the reaction, the solvent was distilled off under reduced pressure. To the obtained residue were added 26.4 g of (±)-trans-3-bromo-6-cyano-3,4-dihydro-2,2-dimethyl-2H-1-benzopyran-4-ol and 120 ml of chloroform previously dried over calcium chloride and the whole mixture was dissolved. To the reaction mixture was added dropwise 34 ml of pyridine under stirring and water-cooling at 15° C. for 10 minutes. The solvent was distilled off under reduced pressure, to the residue was added water and stirred. The separated semisolid product was washed with water and dried under reduced pressure at ordinary temperature. To the residue was added 830 ml of ethyl acetate, the mixture was boiled and then cooled. The obtained crystals were collected by filtration to give 20.7 g of trans-3-bromo-6-cyano-3,4-dihydro-2,2-dimethyl-4-(N-3-nitrobenzenesulfonyl-L-prolyloxy)-2H-1-benzopyran as a sparingly soluble diastereomer compound, melting at 228°–229° C. with decomposition, $[\alpha]^{23}_D = +41.4°$ (c=1, CHCl$_3$)

The above mentioned filtrate was concentrated under reduced pressure and the residue was boiled with a mixture of 150 ml of ethyl acetate and 150 ml of ethanol for several minutes. The reaction mixture was cooled to give 23.0 g of the mentioned above compound as a readily soluble diastereomer compound, melting at 171°–174° C., $[\alpha]^{23}_D = -77.3°$ (c=1, CHCl$_3$)

(2) To a suspension of 20.9 g of the sparingly soluble diastereomer compound and 120 ml of dioxane was added an aqueous solution of 5.0 g of sodium hydroxide in 25 ml of water under stirring at room temperature. After stirring in a water bath at 40°–45° C. for 40 minutes, the solvent was distilled off under reduced pressure. To the residue was added ice-water under stirring to precipitate a crude epoxide compound as white crystals. After the crystals were collected by filtration and dried, the crystals were recrystallized from hexane-ethanol (3:2) to give 6.8 g of (−)-6-cyano-3,4-dihydro-2,2-dimethyl-3,4-epoxy-2H-1-benzopyran, melting at 144°–145° C., $[\alpha]^{23}_D = -86.2°$ (c=1, CH$_2$Cl$_2$)

A similar procedure as in the above mentioned example 1 (2) was performed by using 22.7 g of the readily soluble diastereomer compound to give 6.2 g of (+)-6-cyano-3,4-dihydro-2,2-dimethyl-3,4-epoxy-2H-1-benzopyran, melting at 142°–144° C., $[\alpha]^{23}_D = +87.0°$ (c=1, CH$_2$Cl$_2$)

After filtering each of two crude epoxide compounds, each of the obtained alkali filtrates was respectively acidified with concentrated hydrochloric acid to recover 10.3 g of N-3-nitrobenzenesulfonyl-L-proline as white or light yellow crystals [from the filtrate of (−)-epoxide] and 11.1 g of N-3-nitrobenzenesulfonyl-L-proline [from the filtrate of (+)-epoxide], melting at 155°–157° C., $[\alpha]^{23}_D = -71.3°$ (c=1, CHCl$_3$), respectively.

EXAMPLE 2

(1) A similar procedure as in Example 1(1) was performed by using 6.7 g of N-4-nitrobenzenesulfonyl-L- proline and 5.7 g of (±)-trans-3-bromo-6-cyano-3,4-dihydro-2,2-dimethyl-2H-1-benzopyran-4-ol to give 4.72 g of trans-3-bromo-6-cyano-3,4-dihydro-2,2-dimethyl-4-(N-4-nitrobenzenesulfonyl-L-prolyloxy)-2H-1-benzopyran as a sparingly soluble diastereomer compound, melting at 226.5°–227° C. with decomposition, $[\alpha]^{23}_D = +44.7°$ (c=1, CHCl$_3$) and 5.01 g of the corresponding readily soluble diastereomer compound, melting at 177°–180° C., $[\alpha]^{23}_D = -93.2°$ (c=1, CHCl$_3$), respectively.

(2) A similar procedure as in Example 1(2) was performed by using 4.43 g of the obtained sparingly soluble diastereomer compound to give 1.3 g of (−)-6-cyano-3,4-dihydro-2,2-dimethyl-3,4-epoxy-2H-1-benzopyran, melting at 143°–144° C., $[\alpha]^{23}_D = -89.7°$ (c=1, CH$_2$Cl$_2$) and then a similar recovery procedure as in Example 1(2) was performed to recover 1.94 g of N-4-nitrobenzenesulfonyl-1-proline, melting at 147°–149° C.

On the other hand, a similar procedure as in Example 1(2) was performed by using 4.84 g of the obtained readily soluble diastereomer compound to give 1.42 g of (+)-6-cyano-3,4-dihydro-2,2-dimethyl-3,4-epoxy-2H-1-benzopyran, melting at 143°–144.5° C., $[\alpha]^{23}_D = +85.9°$ (c=1, CH$_2$Cl$_2$) and then a similar recovery procedure as in Example 1(2) was performed to recover 2.28 g of N-4-nitrobenzenesulfonyl-L-proline.

EXAMPLE 3

To a solution of 6.6 g of N-4-toluenesulfonyl-L-proline in 20 ml of chloroform was added 3.3 ml of thionyl chloride and refluxed under heating for 15 minutes. The solvent was distilled off under reduced pressure and to the residue was added 20 ml of chloroform. To the solution was added 4.4 g of (±)-trans-3-bromo-6-cyano-3,4-dihydro-2,2-dimethyl-2H-1-benzopyran-4-ol, and 7.0 ml of pyridine was added dropwise under water-cooling at 15° C. and the mixture then was stirred at 40° C. for 60 minutes. After the solvent was distilled off under reduced pressure, to the residue was added water and ethyl acetate under stirring. After the organic layer was washed with a diluted aqueous potassium carbonate solution and an aqueous sodium chloride solution, the organic layer was concentrated. The residue was recrystallized from hexane-ethyl acetate (1:1) to give 1.6 g of trans-3-bromo-6-cyano-3,4-dihydro-2,2-dimethyl-4-(N-4-toluenesulfonyl-L-prolyloxy)-2H-1-benzopyran as a sparingly soluble diastereomer compound, melting at 162°–169° C., $[\alpha]^{23}_D = -108.9°$ (c=1, CHCl$_3$)

To 1.44 g of the obtained sparingly soluble diastereomer compound was added 9 ml of dioxane and 8 ml of 1N sodium hydroxide and the mixture was stirred at 40° C. for 25 minutes. The solvent was distilled off under reduced pressure and to the residue was added ice-water. The obtained crystals were collected by filtration and dried to give a crude (+)-6-cyano-3,4-dihydro-2,2-dimethyl-3,4-epoxy-2H-1-benzopyran. The recrystallization from hexane-ethanol (2:1) gave 0.34 g of the corresponding purified sample, melting at 139°–143° C., $[\alpha]^{23}_D = +83.6°$ (c=1, CH$_2$Cl$_2$)

EXAMPLE 4

A similar procedure as in Example 3 was performed by using N-4-chlorobenzenesulfonyl-L-proline to give trans-3-bromo-6-cyano-3,4-dihydro-2,2-dimethyl-4-(N-4-chlorobenzenesulfonyl-L-prolyloxy)-2H-1-benzopyran as a sparingly soluble diastereomer compound, melting at 177.5°–179.5° C., $[\alpha]^{23}_D = +21.2°$ (c=1, CHCl$_3$) (when recrystallized from ethanol:ethyl acetate=5:1)

What is claimed is:

1. A method for preparing an optically active 3,4-dihydro-3,4-epoxy-2H-1-benzopyran compound of the formula (II)

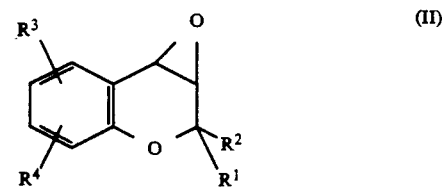

wherein R$^1$ and R$^2$ are the same or different, and each is hydrogen, C$_{1-6}$ alkyl, or R$^1$ and R$^2$ combinedly together form C$_{2-5}$ alkylene; R$^3$ and R$^4$ are the same or different, and each is hydrogen, halogen, nitro, cyano, amino, C$_{1-6}$ alkyl, halo-C$_{1-6}$ alkyl, C$_{1-6}$ alkoxy, halo-C$_{1-6}$ alkoxy, carboxy, C$_{1-6}$ alkoxycarbonyl, formyl, C$_{2-6}$ alkanoyl, halo-C$_{2-6}$ alkanoyl, benzoyl, naphthoyl, phenyl-C$_{2-6}$ alkanoyl, naphthyl-C$_{2-6}$ alkanoyl, formylamino, C$_{2-6}$ alkanoylamino, benzoylamino, naphthoylamino, phenyl-C$_{2-6}$ alkanoylamino, naphthyl-C$_{2-6}$ alkanoylamino, carbamoyl, C$_{1-6}$ alkylcarbamoyl, di-C$_{1-6}$ alkylcarbamoyl, C$_{1-6}$ alkylthio, halo-C$_{1-6}$ alkylthio, C$_{1-6}$ alkylsulfinyl, halo-C$_{1-6}$ alkylsulfinyl, phenylsulfinyl, naphthylsulfinyl, C$_{1-6}$ alkylsulfonyl, halo-C$_{1-6}$ alkylsulfonyl, phenylsulfonyl, naphthylsulfonyl, sulfamoyl, C$_{1-6}$ alkyl-sulfamoyl, di-C$_{1-6}$ alkylsulfamoyl, in which the term "phenyl", "naphthyl", "benzoyl" and "naphthoyl" include substituted phenyl, substituted naphthyl, substituted benzoyl and substituted naphthoyl by at least one substituent selected from the group consisting of halogen, hydroxy, amino, cyano, C$_{1-6}$ alkyl, C$_{1-6}$ alkoxy and trifluoromethyl on the ring, which comprises subjecting a compound of the formula (I):

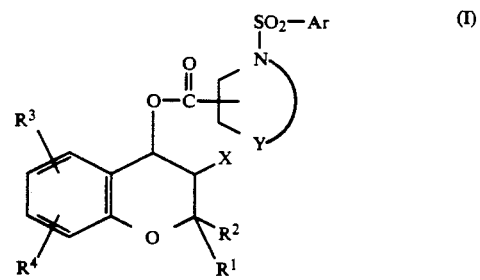

wherein Ar is phenyl, naphthyl, thienyl, furyl, pyridyl, or substituted phenyl, substituted naphthyl, substituted thienyl, substituted furyl and substituted pyridyl by at least one substituent selected from the group consisting of halogen, hydroxy, nitro, C$_{1-6}$ alkyl, C$_{1-6}$ alkoxy and trifluoromethyl; Y is —N(R)(CH$_2$)$_n$—, —O—(CH$_2$)$_m$—, —S—(CH$_2$)$_p$—, —(CH$_2$)$_q$— (wherein R is hydrogen, C$_{1-6}$ alkyl, phenyl, naphthyl, phenyl-C$_{1-6}$ alkyl and naphthyl-C$_{1-6}$ alkyl; each of n, m and p respectively is integer of 2 to 3 and q is integer of 1 to 3); X is bromine, chlorine or iodine; and other symbols are as defined above; and an optically active compound thereof to cyclization by hydrolysis.

2. A compositions comprising a compound of the formula (I) an inert carrier

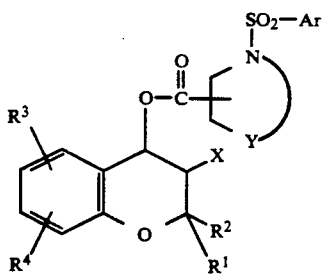

(I)

wherein $R^1$ and $R^2$ are the same or different, and each is hydrogen, $C_{1-6}$ alkyl, or $R^1$ and $R^2$ combinedly together form $C_{2-5}$ alkylene; $R^3$ and $R^4$ are the same or different, and each is hydrogen, halogen, nitro, cyano, amino, $C_{1-6}$ alkyl, halo-$C_{1-6}$ alkyl, $C_{1-6}$ alkoxy, halo-$C_{1-6}$ alkoxy, carboxy, $C_{1-6}$ alkoxycarbonyl, formyl, $C_{2-6}$ alkanoyl, halo-$C_{2-6}$ alkanoyl, benzoyl, naphthoyl, phenyl-$C_{2-6}$ alkanoyl, naphthyl-$C_{2-6}$ alkanoyl, formylamino, $C_{2-6}$ alkanoylamino, benzoylamino, naphthoylamino, phenyl-$C_{2-6}$ alkanoylamino, naphthyl-$C_{2-6}$ alkanoylamino, carbamoyl, $C_{1-6}$ alkylcarbamoyl, di-$C_{1-6}$ alkylcarbamoyl, $C_{1-6}$ alkylthio, halo-$C_{1-6}$ alkylthio, $C_{1-6}$ alkylsulfinyl, halo-$C_{1-6}$ alkylsulfinyl, phenylsulfinyl, naphthylsulfinyl, $C_{1-6}$ alkylsulfonyl, halo-$C_{1-6}$ alkylsulfonyl, phenylsulfonyl, naphthylsulfonyl, sulfamoyl, $C_{1-6}$ alkylsulfamoyl, di-$C_{1-6}$ alkylsulfamoyl, in which the term "phenyl", "naphthyl", "benzoyl" and "naphthoyl" include substituted phenyl, substituted naphthyl, substituted benzoyl and substituted naphthoyl by at least one substituent selected from the group consisting of halogen, hydroxy, amino, cyano, $C_{1-6}$ alkyl, $C_{1-6}$ alkoxy and trifluoromethyl on the ring; Ar is phenyl, naphthyl, thienyl, furyl, pyridyl, or substituted phenyl, substituted naphthyl, substituted thienyl, substituted furyl and substituted pyridyl by at least one substituent selected from the group consisting of halogen, hydroxy, nitro, $C_{1-6}$ alkyl, $C_{1-6}$ alkoxy and trifluoromethyl; Y is —N(R)(CH$_2$)$_n$—, —O—(CH$_2$)$_m$—, —S—(CH$_2$)$_p$—, —(CH$_2$)$_q$— (wherein R is hydrogen, $C_{1-6}$ alkyl, phenyl, naphthyl, phenyl—$C_{1-6}$ alkyl and naphthyl—$C_{1-6}$ alkyl; each of n, m and p respectively is integer of 2 to 3 and q is integer of 1 to 3); X is bromine, chlorine or iodine and an optically active compound thereof, in making of an optically active 3,4-dihydro-3,4-epoxy-2H-1-benzopyran compound of the formula (II)

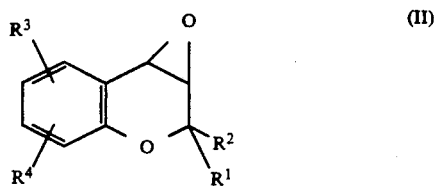

(II)

wherein each symbols is as defined above, and further an optically active benzopyran compound.

* * * * *